(12) United States Patent
Min

(10) Patent No.: US 10,940,249 B2
(45) Date of Patent: Mar. 9, 2021

(54) METHODS AND SYSTEMS FOR REDUCING THE RISK OF BACTERIAL CONTAMINATION IN COLLECTED PLATELETS

(71) Applicant: Fenwal, Inc., Lake Zurich, IL (US)

(72) Inventor: Kyungyoon Min, Kildeer, IL (US)

(73) Assignee: FENWAL, INC., Lake Zurich, IL (US)

( * ) Notice: Subject to any disclaimer, the term of this patent is extended or adjusted under 35 U.S.C. 154(b) by 0 days.

(21) Appl. No.: 16/404,347

(22) Filed: May 6, 2019

(65) Prior Publication Data

US 2019/0255233 A1     Aug. 22, 2019

Related U.S. Application Data

(62) Division of application No. 15/492,169, filed on Apr. 20, 2017, now Pat. No. 10,328,189.

(60) Provisional application No. 62/325,809, filed on Apr. 21, 2016.

(51) Int. Cl.
    *A61M 1/02*         (2006.01)
    *A61M 1/36*         (2006.01)
    *A61M 1/38*         (2006.01)
    *B04B 5/04*         (2006.01)
    (Continued)

(52) U.S. Cl.
    CPC .......... *A61M 1/025* (2013.01); *A61M 1/0209* (2013.01); *A61M 1/0236* (2014.02); *A61M 1/0272* (2013.01); *A61M 1/3659* (2014.02); *A61M 1/3693* (2013.01); *A61M 1/38* (2013.01); *B04B 5/0442* (2013.01); *B04B 11/02* (2013.01); *C12N 5/0644* (2013.01); *A61M 2202/0415* (2013.01); *A61M 2202/0427* (2013.01); *A61M 2202/0429* (2013.01);
(Continued)

(58) Field of Classification Search
CPC .. A61M 1/025; A61M 1/0209; A61M 1/0236; A61M 1/3659; A61M 1/38; A61M 2202/0415; A61M 2202/0427; A61M 2202/0429; A61M 2205/3337; A61M 2205/50; A61M 2205/502; A61M 2205/52; B04B 5/0442; B04B 11/02; C12N 5/0644
See application file for complete search history.

(56) References Cited

U.S. PATENT DOCUMENTS 5,316,667 A    5/1994   Brown et al.
5,868,696 A    2/1999   Giesler et al.
(Continued)

FOREIGN PATENT DOCUMENTS

WO    WO 2001/008546 A2    2/2001

OTHER PUBLICATIONS

Eder et al., "Limiting and detecting bacterial contamination of apheresis platelets: inlet-line diversion and increased culture volume improve component safety", Aug. 2009. Transfusion, vol. 49, pp. 1554-1563. (Year: 2009).*

(Continued)

*Primary Examiner* — Timothy C Cleveland
(74) *Attorney, Agent, or Firm* — Cook Alex Ltd.

(57) ABSTRACT

Methods and systems for reducing bacterial contamination of platelets are disclosed. The methods and systems disclosed herein provide for the processing of a pre-determined volume of whole blood so as to reduce the risk that platelets separated and collected from the whole blood have a reduced risk of bacterial contamination.

14 Claims, 7 Drawing Sheets

(51) Int. Cl.
*B04B 11/02* (2006.01)
*C12N 5/078* (2010.01)

(52) U.S. Cl.
CPC . *A61M 2205/3337* (2013.01); *A61M 2205/50* (2013.01); *A61M 2205/502* (2013.01); *A61M 2205/52* (2013.01)

(56) References Cited

U.S. PATENT DOCUMENTS

2007/0243990 A1* 10/2007 Kolenbrander ..... A61M 1/3644
494/37
2014/0378290 A1 12/2014 Kimura

OTHER PUBLICATIONS

Eder, Anne F., et al., "Limiting and detecting bacterial contamination of apheresis platelets: inlet-line diversion and increased culture volume improve component safety", Aug. 2009, Transfusion, vol. 49, pp. 1554-1563.
Extended Suropean Search Report for International Application No. 17167327.0, dated Jul. 26, 2017.

* cited by examiner

METHODS AND SYSTEMS FOR REDUCING THE RISK OF BACTERIAL CONTAMINATION IN COLLECTED PLATELETS

CROSS REFERENCE TO RELATED APPLICATIONS

This is a divisional application of U.S. patent application Ser. No. 15/492,169, now U.S. Pat. No. 10,328,189, filed Apr. 20, 2017 which claims the benefit of and priority to U.S. Provisional Application No. 62/325,809, filed Apr. 21, 2016 both of which are incorporated herein by reference in their entireties.

FIELD OF INVENTION

The present disclosure is directed to methods and systems for reducing the risk of bacterial contamination in collected platelets. More particularly, the present disclosure is directed to methods and systems for reducing bacterial contamination in collected platelets, such as apheresis platelets, by withdrawing a pre-determined volume of blood from the donor and returning the same to the donor prior to platelet collection.

BACKGROUND

Various blood processing systems now make it possible to collect particular blood components, rather than whole blood, from a blood source. Typically, in such systems, whole blood is drawn from a blood source, such as a human donor, the particular blood component is separated, removed, and collected, and the remaining blood components are returned to the blood source. Removing only particular components is advantageous when the blood source is a human donor or patient, because potentially less time is needed for the donor's body to return to pre-donation levels, and donations can be made at more frequent intervals than when whole blood is collected. This increases the overall supply of blood components, such as plasma and platelets that are available for transfusion and/or therapeutic treatment.

Platelets are collected from healthy donors and administered to patients whose ability to produce platelets has been compromised by chemotherapy of other conditions. In order to collect platelets, whole blood is first separated into its constituent components, including platelets, most typically by centrifugation. Centrifugal separators are well known and allow the platelets to be collected while returning other components, e.g., red blood cells, plasma, back to the donor in a process known as "apheresis." An example of an automated apheresis device is the AMICUS® separator sold by Fenwal, Inc. of Lake Zurich, Ill., which is an affiliate of Fresenius Kabi AG of Bad Homburg, Germany, and which is described in greater detail in U.S. Pat. No. 5,868,696 and International Application Publication WO2013/048984, both of which are incorporated herein by reference.

Using an automated apheresis device, the whole blood is obtained from a source such as a healthy human donor by accessing the vascular system of the donor with a phlebotomy or venipuncture needle. As will be described in greater detail below, the hollow needle is in flow communication with a disposable tubing and container fluid circuit or kit that is configured for use with the apheresis device. Prior to venipuncture, the donor's skin is typically cleaned or otherwise prepared to remove bacteria that may reside on the surface of the donor's skin. Notwithstanding recent improvements in skin preparation, some residual bacteria may remain on the skin. For example, the so-called "skin plug," (the piece of skin that is dislodged by the puncturing action of the needle) may be carried into the blood and potentially introduce bacteria into the blood being withdrawn from the donor. In addition, bacteria present on the surface of the donor's skin may be carried into the blood independent of a dislodged skin plug. Eventually, the bacteria associated can find its way into the collected blood product, i.e., platelets.

In an effort to diminish the potential risk of bacterial contamination of the whole blood and more particularly, the collected component derived from the whole blood, "sample diversion" systems have been developed which divert the initial flow of blood to a satellite pouch of limited volume. This sample pouch serves the dual purpose of (a) providing a small volume of the donor's whole blood which can be used for testing and analysis and (b) diverting the initial flow of blood which is likely to contain the skin plug or bacteria away from the separation and collection containers and the flow paths leading thereto. Such sample diversion systems are described in U.S. Pat. Nos. 7,044,941, 6,520,948, 6,387,086 and 8,517,970, all of which are incorporated herein by reference.

While the sample diversion systems described in the above-identified patents have been very effective in reducing the possibility of bacterial contamination of collected blood platelets, there is still a moderate risk that bacteria residing on the skin of the donor may not be diverted to the sample pouch with the initial volume of whole blood, and instead be carried over to the separation chambers and collection containers of the disposable fluid circuit. One way to ensure greater confidence that the skin plug and any associated bacteria are diverted to the sample pouch would be to increase the volume of the initial flow of blood that is collected in the sample pouch. However, doing so would increase the blood loss in the donor as the whole blood collected in the sample pouch is not processed and is, in effect, "waste."

Thus, it would be desirable to provide a method and system that further decreases the risk of bacterial contamination in collected platelets without increasing blood loss in the donor and without adding substantial time to the platelet collection procedure. The methods and systems described herein address this need.

SUMMARY

In one aspect, the present disclosure is directed to a method for reducing the risk of bacterial contamination in collected blood platelets. The method includes the steps of inserting a needle of a blood processing circuit into a donor to access the vascular system of the donor; withdrawing a pre-determined volume of whole blood from the donor; introducing the pre-determined volume of said whole blood into at least a portion of the blood processing circuit; returning at least substantially the pre-determined volume to said donor; and withdrawing a second volume of whole blood from the donor.

In another aspect, the present disclosure is directed to an automated system for the collection of blood platelets. The system includes a disposable fluid circuit configured for the flow of whole blood and/or a separated blood component through the circuit. The circuit includes at least one venipuncture needle for accessing the vascular system of a donor and a blood separation chamber for separating whole blood into one or more components. The system further includes a reusable hardware device configured to receive a portion of the disposable fluid circuit. The hardware device includes a separator element, a pump for withdrawing whole blood from a donor, a pump for removing one or more blood components from said separation chamber, valves for selectively diverting and directing liquid flow, and a controller. The controller is configured to, among other things, (i) monitor the volume of blood withdrawn from the donor; (ii) selectively control the pumps to effect movement of blood and blood components through the disposable fluid circuit; (iii) effect withdrawal a first pre-determined volume of whole blood from a donor and a second volume of whole blood from a donor; and (iv) effect collection of platelets only from the second volume of whole blood.

DETAILED DESCRIPTION OF THE EMBODIMENTS

As noted above, the present disclosure is directed to methods and systems for collecting blood platelets with a reduced risk of bacterial contamination. The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
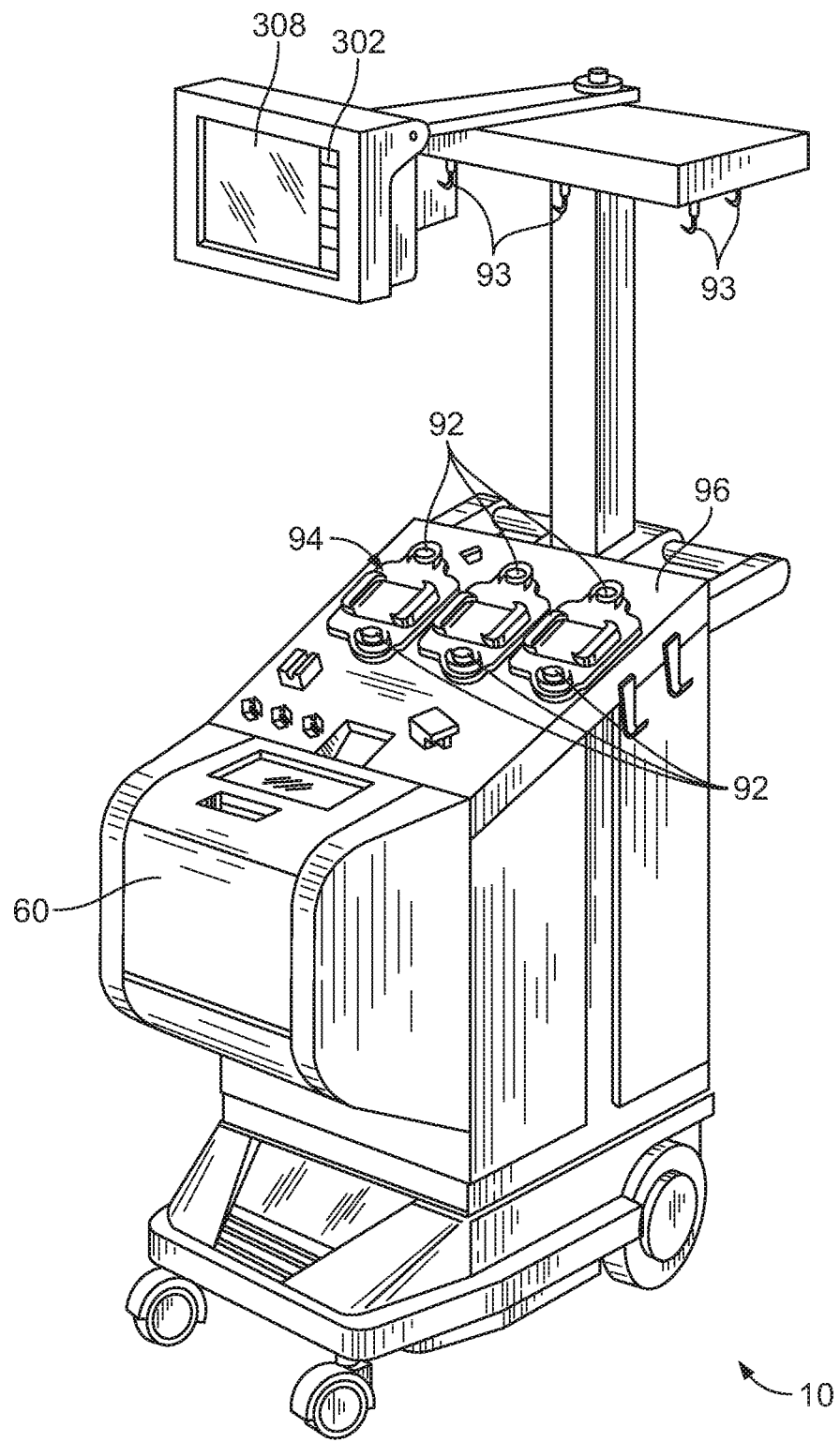
FIG. 1 is a perspective view of a blood separation device suitable for performing the methods in accordance with the present disclosure.

Blood processing systems according to the present disclosure include a separation device, which may be variously provided without departing from the scope of the present disclosure. FIG. 1 depicts one example of a durable separation device 10 that may be employed in blood processing systems and methods according to the present disclosure. The separation device 10 may be provided according to known design, such as the system currently marketed as the AMICUS® separator sold by Fenwal, Inc. of Lake Zurich, Ill., which is an affiliate of Fresenius Kabi AG of Bad Homburg, Germany, as described in greater detail in U.S. Pat. No. 5,868,696 and International Application Publication No. WO 2013/048984, both of which are incorporated herein by reference in their entireties. The separation device 10 can be used for processing various fluids, but is particularly well suited for processing whole blood and for separating blood platelets from the other whole blood components and collecting the platelets for later administration to a patient.

A. The Fluid Circuit

Figure 2:
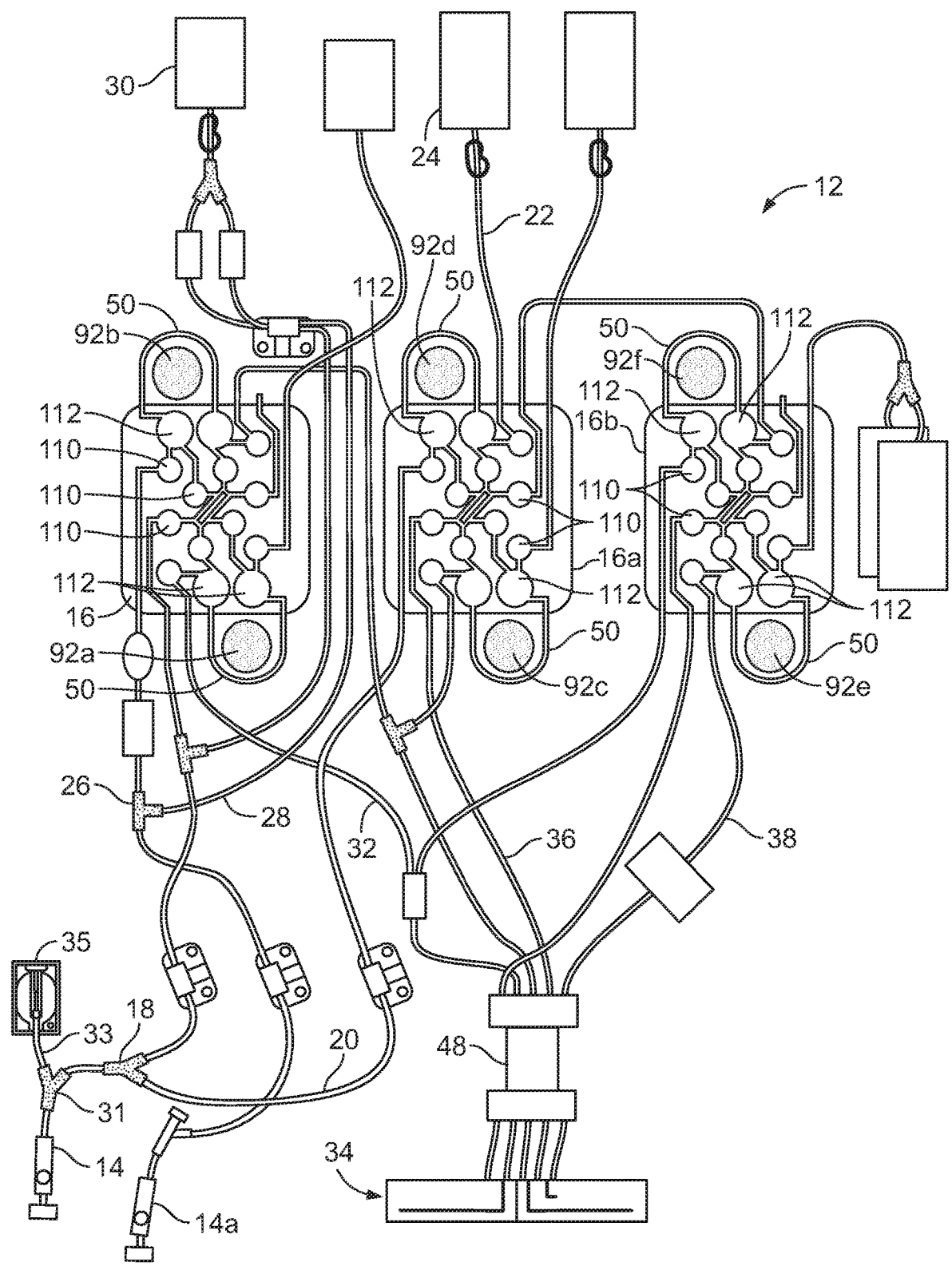
FIG. 2 is a diagrammatic view of one embodiment of a disposable fluid circuit that may be used in combination with the separation device of FIG. 1.
Figure 2A:
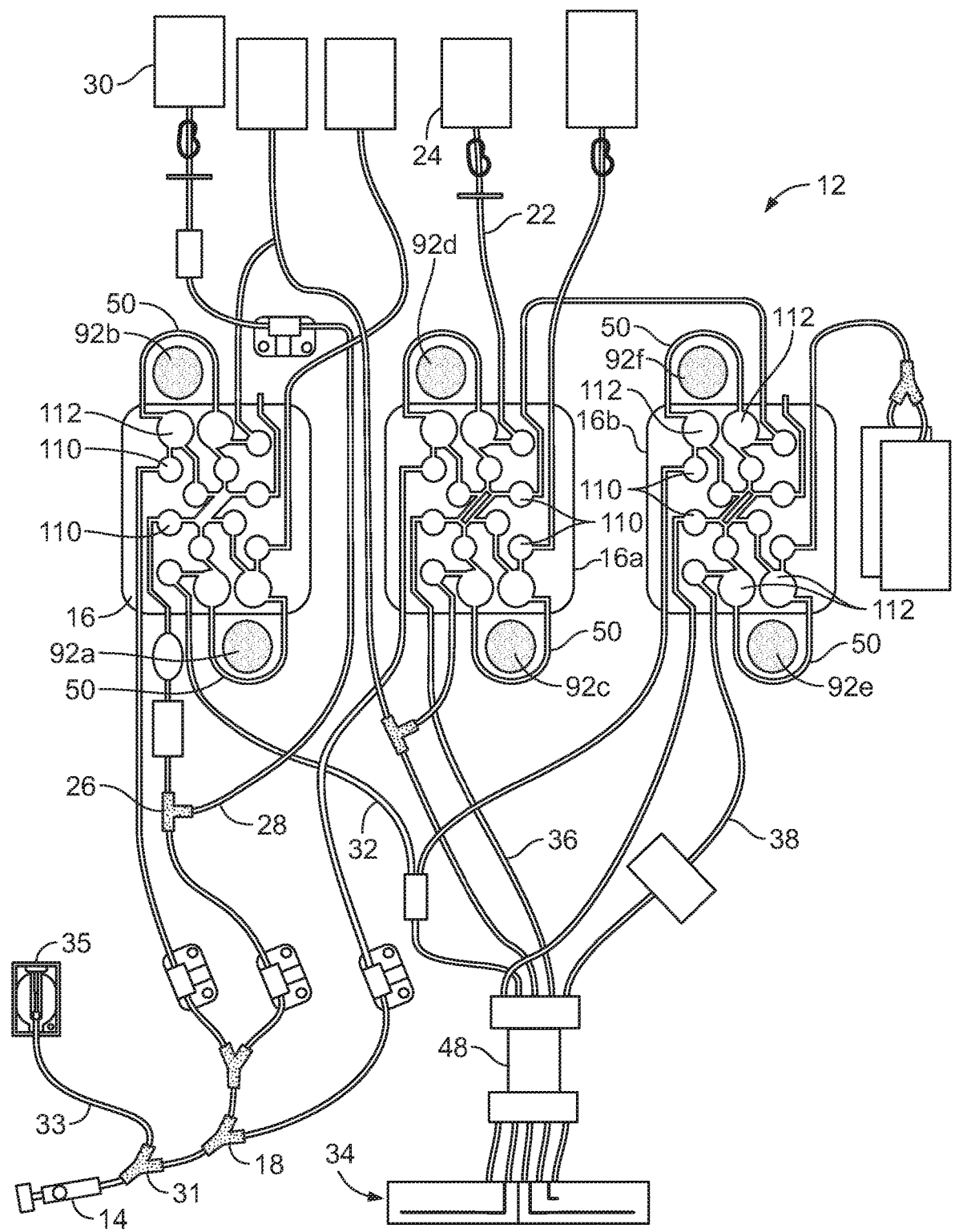
FIG. 2A is a diagrammatic view of another embodiment of a disposable fluid circuit that may be used in combination with the separation device of FIG. 1.

Each of FIGS. 2 and 2A illustrates a disposable fluid circuit 12 that may be used in combination with the separation device 10 of FIG. 1 to provide a blood processing system. The fluid circuit 12 includes a variety of tubing and a number of components, only some of which will be described herein in greater detail. It should be understood that FIGS. 2 and 2A illustrate examples of a fluid circuit which may be used in combination with the separation device 10 of FIG. 1 and differently configured fluid circuits may also be employed without departing from the scope of the present disclosure.

The fluid circuit 12 shown in FIG. 2 is a "double needle" system, which includes a pair of blood source access devices 14 and 14a (e.g., venipuncture needles) for fluidly connecting a blood source with the fluid circuit 12. The fluid circuit 12 shown in FIG. 2A is a "single needle" system which includes a single blood source access device 14. In one embodiment, the blood source may be a human donor. The blood source access devices 14 and 14a are connected by tubing to a cassette 16, which will be described in greater detail herein. As shown in FIGS. 2 and 2A, fluid circuit 12 includes a plurality of cassettes. Blood source access device 14 is used to draw blood from the blood source into the fluid circuit 12 and is connected to, for example, the left cassette 16 by a y-connector 18. The other leg of the y-connector 18 is connected to tubing 20 which leads to a middle cassette 16a. The tubing 20 is connected, through the middle cassette 16a, to additional tubing 22, which includes a container access device (e.g., a sharpened cannula or spike connector, not shown) for accessing the interior of an anticoagulant container 24. During a blood processing and/or separation operation, anticoagulant from the anticoagulant container may be added to the blood from the blood source at the y-connector 18 prior to entering the left cassette 16. As shown in FIG. 2, access device 14 and the tubing leading from it may also include a further branch member 31 and a sample pouch 35 attached to tube 33 extending from one leg of branch member 31.

With reference to FIG. 2, the other blood source access device 14a is used to deliver or return blood, a blood component, (and/or some other replacement fluid to the blood source) and is also connected to the left cassette 16 by a y-connector 26. The other leg of the y-connector 26 is connected to tubing 28 connected at its other end to a container access device 30. Although not illustrated, the container access device may be associated with a container 30 having an amount of fluid (e.g., saline) to be used to prime the flow circuit 12 and/or delivered to the blood source via the blood source access device 14a. In the fluid circuit 12 of FIG. 2A, source access device 14 is used to deliver and return blood or blood component to the source (donor).

Left cassette 16 also includes tubing 32 which is connected to a blood separation chamber 34 of the flow circuit 12 for flowing anticoagulated blood thereto. The blood processing chamber 34 separates the blood into its constituent components (e.g., red blood cells and platelet-rich plasma, as will be described in greater detail herein) and returns the blood components to the flow circuit 12. In one embodiment, cellular blood components are returned to the middle cassette 16a of the fluid circuit 12 from the blood processing chamber 34 via tubing 36, while platelet-rich plasma is returned to a right cassette 16b of the flow circuit 12 from the blood separation chamber 34 via tubing 38, from where it may be pumped back into a second sub-chamber (described below) of blood separation chamber 34 for further processing into platelets and platelet-poor plasma. The cellular blood components may be pumped to the left cassette 16, where they are returned to the blood source (i.e., donor). Platelet-poor plasma may be pumped back to middle cassette 16a for return to the blood source and/or it may be pumped into a container (not shown). The destination of the fluids passing through the cassettes depends upon the actuation of the various valves of the cassettes, as will be described in greater detail herein. The various tubing connected to the blood separation chamber 34 is bundled in an umbilicus 48, also described in greater detail below.

Additional tubing may be connected from one port of a cassette to another port of the same cassette, so as to form tubing loops 50 which interact with a fluid flow element or pump 92 to flow fluid through the flow circuit 12, as will be described in greater detail herein.

B. The Centrifuge

The separation device 10 includes a separator such as a centrifuge (not shown) used to centrifugally separate blood components. The separation device 10 may be programmed to separate blood into a variety of components (e.g., platelet-rich plasma and red cells). The centrifuge is of the type shown in U.S. Pat. No. 5,316,667 to Brown et al., which is incorporated herein by reference. The centrifuge includes a bowl (not shown) and a spool 56 (FIG. 3) which are housed within device 10. The centrifuge is housed within the interior of the separation device 10, so a door 60 (FIG. 1) is provided to allow access to the centrifuge for loading and unloading the blood processing chamber 34, as will be described in greater detail herein. The door 60 remains closed during operation to protect and enclose the centrifuge.

When in the loading/unloading position, the spool 56 can be opened by movement at least partially out of the bowl. In this position, the operator wraps the flexible blood processing chamber 34 about the spool 56 (see FIG. 3). Closure of the spool 56 and bowl encloses the chamber 34 for processing. When closed, the spool 56 and bowl are pivoted into the operating position of FIG. 3 for rotation about an axis.

C. The Blood Separation Chamber

Figure 3:
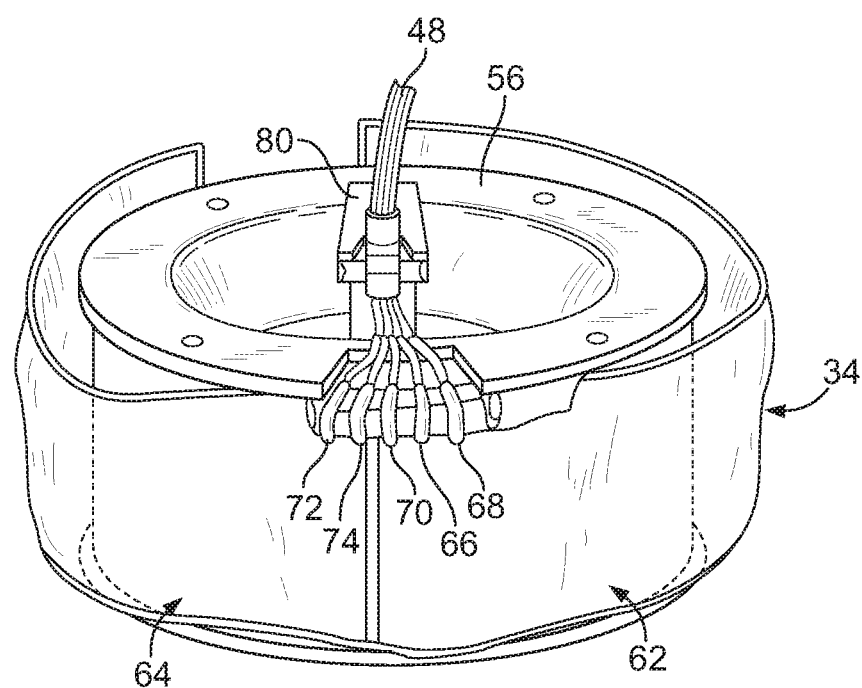
FIG. 3 is a top perspective view of a separator with blood separation chamber mounted thereon.
Figure 4:
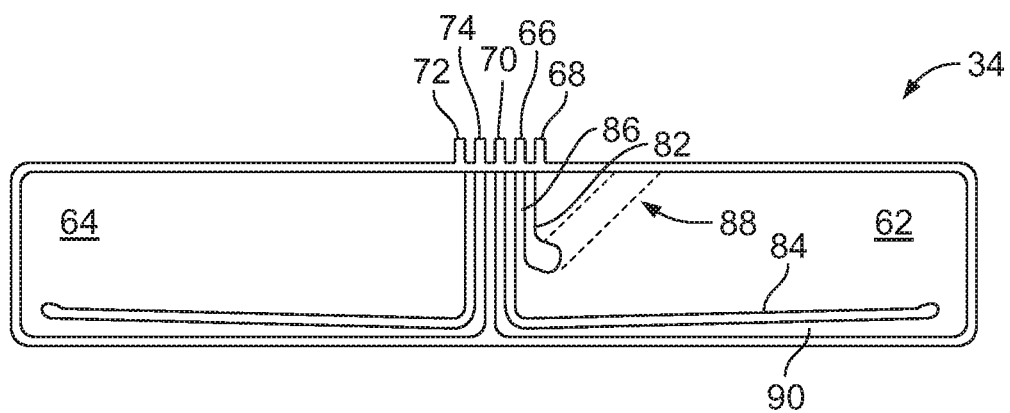
FIG. 4 is a plan view of a the separation chamber of FIG. 3.

FIGS. 3-4 show a representative embodiment of a blood processing chamber 34 which may be used in connection with the methods and systems of the present disclosure. The chamber 34 shown in FIG. 4 allows for either single- or multi-stage processing. When used for multi-stage processing, a first sub-chamber 62 typically separates whole blood into first and second components. Depending on the nature of the separation and/or collection procedure, one of the components may be transferred into a second sub-chamber 64 for further processing.

As shown in FIGS. 3 and 4, ports 66, 68, and 70 may be associated with the first sub-chamber 62. Depending on the particular blood processing procedure, the respective ports may have a different functionality. For example, in a platelet collection procedure, blood enters the first sub-chamber 62 via the port 66 and is separated into red blood cells (i.e., the high density blood component) and platelet-rich plasma (i.e., the low density blood component). The red blood cells are returned to the blood source (via the port 70), while the platelet-rich plasma is then typically conveyed out of the first sub-chamber 62 (via the first outlet port 68) and into the second sub-chamber 64 (via the inlet port 72). In the second sub-chamber 64, the platelet-rich plasma is separated into platelet-poor plasma and platelet concentrate. In a typical platelet collection procedure using the device 10 depicted herein, the platelet-poor plasma is removed from the second sub-chamber 64 (via the outlet port 74), leaving platelet concentrate in the second stage 64 for resuspension and transfer to one or more storage containers.

As best shown in FIG. 3, the tubing umbilicus 48 of the flow circuit 12 is attached to the ports 66, 68, 70, 72, and 74. The umbilicus 48 interconnects the first and second sub-chambers 62 and 64 with each other and with the components of the flow circuit 12 positioned outside of the centrifuge 52. Further details concerning the umbilicus are described in International Application Publication No. WO 2013/048984, previously incorporated by reference.

As shown in FIG. 4, a first interior seal 82 is located between the low density outlet port 68 and the high density outlet port 66. A second interior seal 84 is located between the high density outlet port 66 and the blood inlet port 70. The interior seals 82 and 84 form a fluid passage 86 (an outlet for high density blood components in a therapeutic plasma exchange procedure) and a low density collection region 88 in the first stage 62. The second seal 84 also forms a fluid passage 90 (a blood inlet in a therapeutic plasma exchange procedure) in the first stage 62.

D. The Pumps and Cassettes

Blood entering the blood separation chamber 34 is pumped by one or more pumps 92 of the separation device 10 (FIGS. 1 and 2) acting upon one or more of the tubing loops 50 extending from the cassettes 16-16b of the flow circuit 12 (FIGS. 2 and 2A). A typical cassette 16 is illustrated in greater detail in FIGS. 5 and 6, while the pumps 92 and associated cassette holder 94 are shown in FIGS. 1 and 7.

Before beginning a given blood processing and collection procedure, the operator loads various components of the flow circuit 12 onto the sloped front panel 96 and centrifuge of the separation device 10. As described above, the blood separation chamber 34 and the umbilicus 48 of the flow circuit 12 are loaded into the centrifuge, with a portion of the umbilicus 48 extending outside of the interior of the separation device 10. The sloped front panel 96 of the separation device 10 includes at least one cassette holder 94 (three in the illustrated embodiment), each of which is configured to receive and grip an associated cassette 16-16b of the fluid circuit 12.

Figure 5:
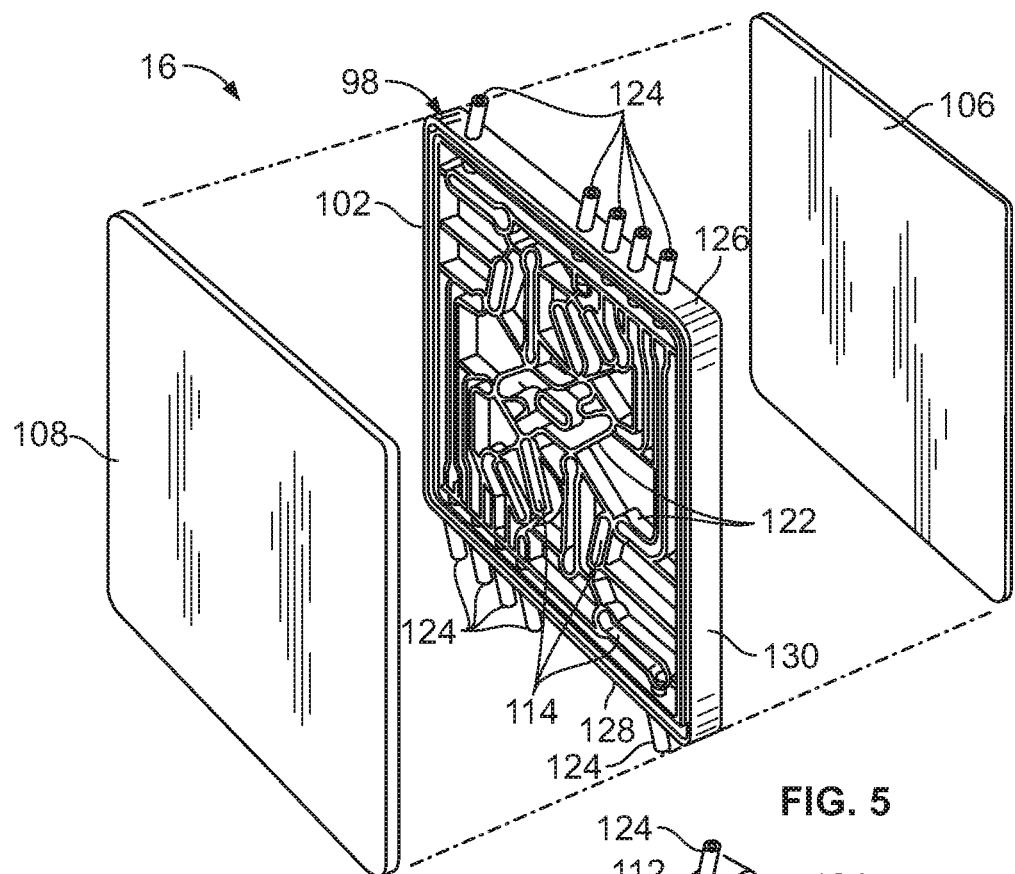
FIG. 5 is an exploded perspective view of a fluid processing cassette of the fluid circuit of FIG. 2.
Figure 6:
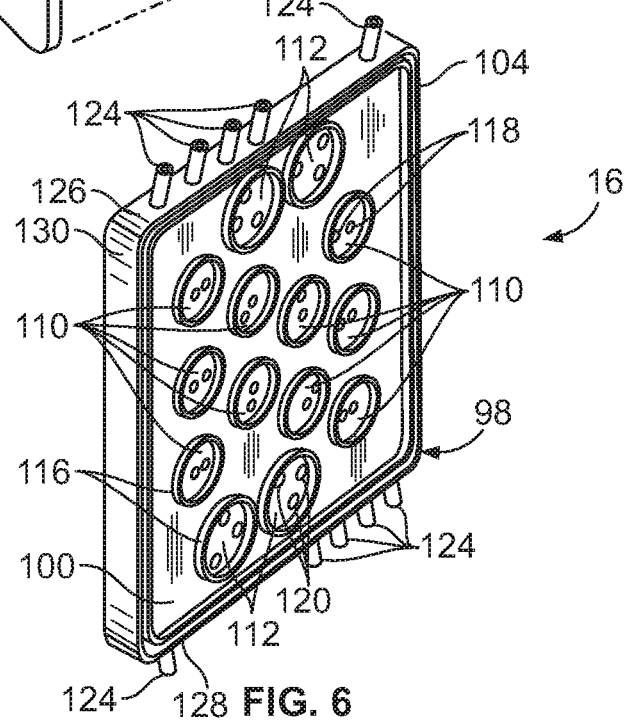
FIG. 6 is a perspective view of a fluid processing cassette of FIG. 5.
Figure 7:
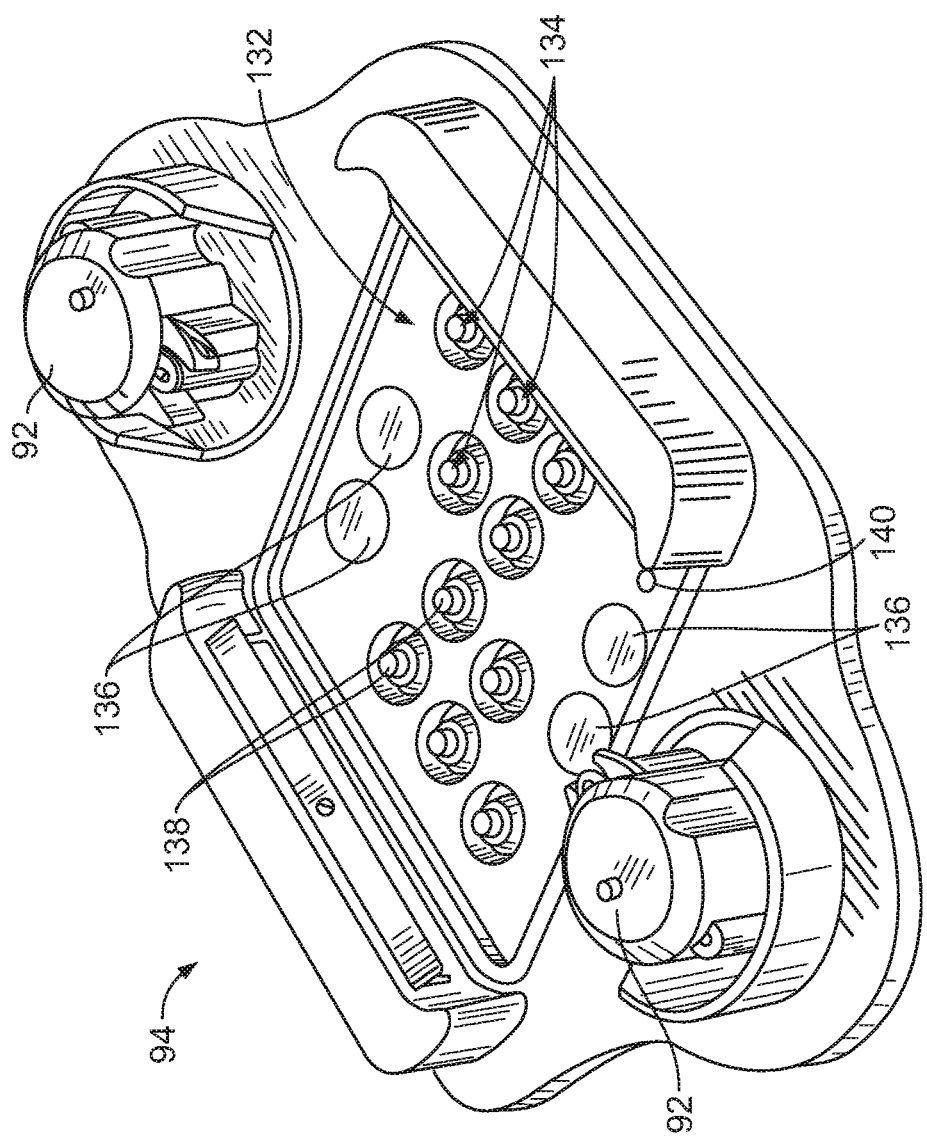
FIG. 7 is a perspective view of a cassette holder of the blood processing device of FIG. 1.

Each cassette 16-16b, one of which is shown in FIGS. 5 and 6, includes an injection molded body 98 that is compartmentalized by an interior wall 100 (FIG. 6) to present or form a topside 102 (FIG. 5) and an underside 104 (FIG. 6). For the purposes of description, the topside 102 is the side of the cassette 16 that, in use, faces away from the separation device 10, while the underside 104 faces towards the separation device 10. A flexible diaphragm 106 overlies and peripherally seals the underside 104 of the cassette 16. A generally rigid upper panel 108 overlies the topside 102 of the cassette 16 and is sealed peripherally and to the raised channel-defining walls in the cassette 16, as described later.

In one embodiment, the cassette 16, the interior wall 100, and the upper panel 108 are made of a rigid medical grade plastic material, while the diaphragm 106 is made of a flexible sheet of medical grade plastic. The upper panel 108 and the diaphragm 106 are sealed about their peripheries to the peripheral edges of the top- and undersides 102, 104 of the cassette 16, respectively.

As further shown in FIGS. 5 and 6, the top and undersides 102, 104 of the cassette 16 contain preformed cavities. On the underside 104 of the cassette 16 (FIG. 5), the cavities form an array of valve stations 110 and an array of pressure sensing stations 112. On the topside 102 of the cassette 16 (FIG. 5), the cavities form an array of channels or paths 114 for conveying liquids. The valve stations 110 communicate with the liquid paths 114 through the interior wall 100 to interconnect them in a pre-determined manner. The sensing stations 112 also communicate with the liquid paths 114 through the interior wall 100 to sense pressures in selected regions. The number and arrangement of the liquid paths 114, the valve stations 110, and the sensing stations 112 can vary but, in the illustrated embodiment, the cassette 16 provides nineteen liquid paths 114, ten valve stations 110, and four sensing stations 112.

The valve and sensing stations 110, 112 resemble shallow wells open on the cassette underside 104 (FIG. 6). Upstanding edges 116 extend from the interior wall 100 and peripherally surround the valve and sensing stations 110, 112. The valve stations 110 are closed by the interior wall 100 on the topside 102 of the cassette 16, except that each valve station 110 includes a pair of through holes or ports 118 in the interior wall 100. The ports 118 each open into selected different liquid paths 114 on the topside 102 of the cassette 16.

The sensing stations 112 are likewise closed by the interior wall 100 on the topside 102 of the cassette 16, except that each sensing station 112 includes three through holes or ports 120 in the interior wall 100 (FIG. 6). The ports 120 open into selected liquid paths 114 on the topside 102 of the cassette 16. These ports 120 channel liquid flow among the selected liquid paths 114 through the associated sensing station 112.

In one embodiment, the flexible diaphragm 106 overlying the underside 104 of the cassette 16 is sealed by ultrasonic welding to the upstanding peripheral edges 116 of the valve and sensing stations 110, 112. This isolates the valve stations 110 and sensing stations 112 from each other and the rest of the system. In an alternative embodiment, the flexible diaphragm 106 can be seated against the upstanding edges 116 by an external positive force applied by the cassette holder 94 against the diaphragm 106. The positive force, like the ultrasonic weld, peripherally seals the valve and sensing stations 110, 112.

The localized application of additional positive force (referred to herein as a "closing force") upon the intermediate region of the diaphragm 106 overlying a valve station 110 serves to flex the diaphragm 106 into the valve station 110. Such closing force is provided by the cassette holder 94, as will be described in greater detail herein. The diaphragm 106 seats against one of the ports 118 to seal the port 118, which closes the valve station 110 to liquid flow. Upon removal of the closing force, fluid pressure within the valve station 110, the application of a vacuum to the outer surface of the diaphragm 106, and/or the plastic memory of the diaphragm 106 unseats the diaphragm 106 from the port 118, opening the valve station 110 to liquid flow.

Figure 8:
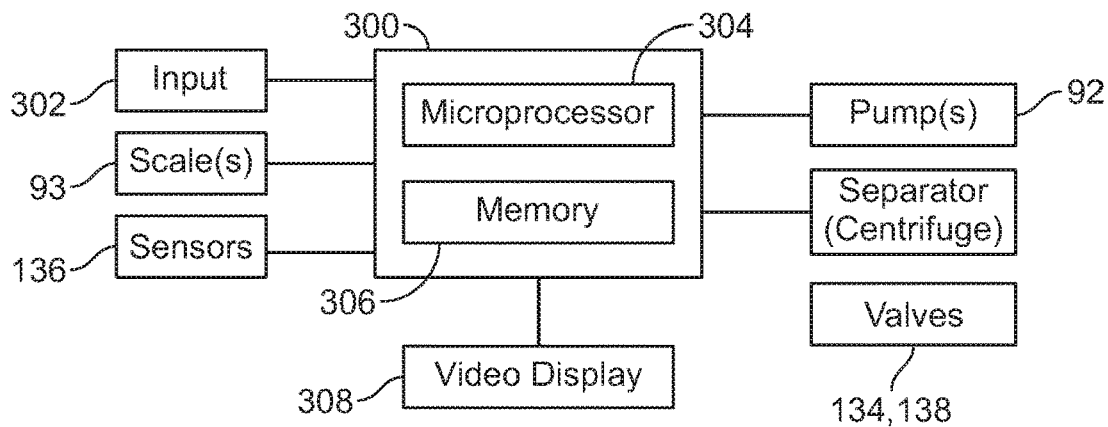
FIG. 8 is a schematic view of the control circuitry, including the controller, of the device of FIG. 1.

Upstanding channel sides or edges 122 rise from the interior wall 100 to peripherally surround and define the liquid paths 114, which are open on the topside 102 of the cassette 16. The liquid paths 114 are closed by the interior wall 100 on the underside 104 of the cassette 16, except for the ports 118, 120 of the valve and sensing stations 110, 112 (FIG. 8). The rigid panel 108 overlying the topside 102 of the cassette 16 is sealed by ultrasonic welding to the upstanding peripheral edges 122, sealing the liquid paths 114 from each other and the rest of the system.

In the illustrated embodiment, pre-molded tube connectors 124 extend out along opposite side edges 126, 128 of each cassette 16. The tube connectors 124 are arranged five on one side edge 126 and five on the other side edge 128. The other side edges 130 of the cassette 16, as illustrated, are free of tube connectors. The tube connectors 124 are associated with external tubing (FIG. 2) to associate the cassettes 16 with the remainder of the flow circuit 12, as described above.

The tube connectors 124 communicate with various interior liquid paths 114, which constitute the liquid paths of the cassette 16 through which a fluid enters or exits the cassette 16. The remaining interior liquid paths 114 of the cassette 16 constitute branch paths that link the liquid paths 114 associated with the tube connectors 124 to each other through the valve stations 110 and sensing stations 112.

Turning now to the cassette holders 94 (FIG. 7), each holder 94 receives and grips one of the cassettes 16-16*b* along the two opposed sides edges 130 in the desired operating position. The cassette holder 94 includes a pair of peristaltic pump stations 92. When the cassette 16 is gripped by the cassette holder 94, tubing loops 50 extending from the cassette 16 (FIG. 2) make operative engagement with the pump stations 92. The pump stations 92 are operated to cause fluid flow through the cassette 16.

The flexible diaphragm 106 covering the underside 104 of the cassette 16 is urged into intimate contact with a valve and sensor array or assembly 132 by the cassette holder 94 (FIG. 1). The valve assembly 132 acts in concert with the valve stations 110 and sensing stations 112 of the cassette 16. The valve assembly includes valve actuators 134 and four pressure sensing transducers 136. The valve actuators 134 and the pressure sensing transducers 136 are mutually arranged in the same layout as the valve stations 110 and sensing stations 112 on the underside 104 of the cassette 16. When the cassette 16 is gripped by the cassette holder 94, the valve actuators 134 align with the cassette valve stations 110. At the same time, the pressure sensing transducers 136 mutually align with the cassette sensing stations 112.

In one embodiment, each valve actuator 134 includes an electrically actuated solenoid pin or piston 138. Each piston 138 is independently movable between an extended position and a retracted position. When in its extended position, the piston 138 presses against the region of the diaphragm 106 that overlies the associated valve station 110. In this position, the piston 138 flexes the diaphragm 106 into the associated valve station 110, thereby sealing the associated valve port 118. This closes the valve station 110 to liquid flow. When in its retracted position, the piston 138 does not apply force against the diaphragm 106. As before described, the plastic memory of the diaphragm 106 may be such that the removal of force is sufficient for the diaphragm to unseats from the valve port 118, thereby opening the valve station 110 to liquid flow. Alternatively, a vacuum may be applied to the diaphragm 106, for example by the vacuum port 140 illustrated in FIG. 9, to actively unseat the diaphragm 106 from the valve port 118.

The pressure sensing transducers 136 sense liquid pressures in the sensing stations 112 of the cassette 16. The sensed pressures are transmitted to a controller of the separation device 10 as part of its overall system monitoring and controlling function.

E. Controller

FIG. 8 is a schematic view of the control unit or "controller" 300 included in device 10 of the present disclosure. The controller 300 may include a microprocessor 304 (which may include multiple physical and/or virtual processors). According to other embodiments, the controller 300 may include one or more electrical circuits designed to carry out the actions described herein. In an embodiment, controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304, may cause the microprocessors 304 to carry out one or more actions as described herein.

As is also illustrated in FIG. 8, controller 300 may be coupled to one or more of the structures described above, for example to receive information (e.g., in the form of signals) from these structures or to provide commands (e.g., in the form of signals) to these structures to control the operation of the structures. As illustrated in FIG. 8, the controller 300 may be coupled to the scales 93 (seen in FIG. 1) that hold solution containers or that are provided to collect separated blood components, the sensors associated with device 10, or more specifically with the cassettes 16, 16a, and 16b, the valve assemblies 132 and the at least one input 302 to receive information from those devices. Additionally, the controller 300 may be coupled to the pumps 92a-f and the separator (centrifuge) drive unit 248 to provide commands to those devices and to control their operation. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel of the device 10, the video display 308 also being coupled to the controller 300. The assembly of the input/touch screen 302 and video display 308 may be one of the afore-mentioned structures to which the controller 300 is coupled from which the controller 300 receives information and to which the controller 300 provides commands.

F. Method and System of Reducing Contamination Risk in Platelets

The method of collecting platelets with a reduced risk of contamination will now be described. The method will be described in the context of device 10, shown and described above, with reference to the method steps set forth in FIG. 9. However, it will be understood that the method is not limited to use with the above-described device, but can be practiced with other devices or systems adapted for automated platelet collection.

Figure 9:
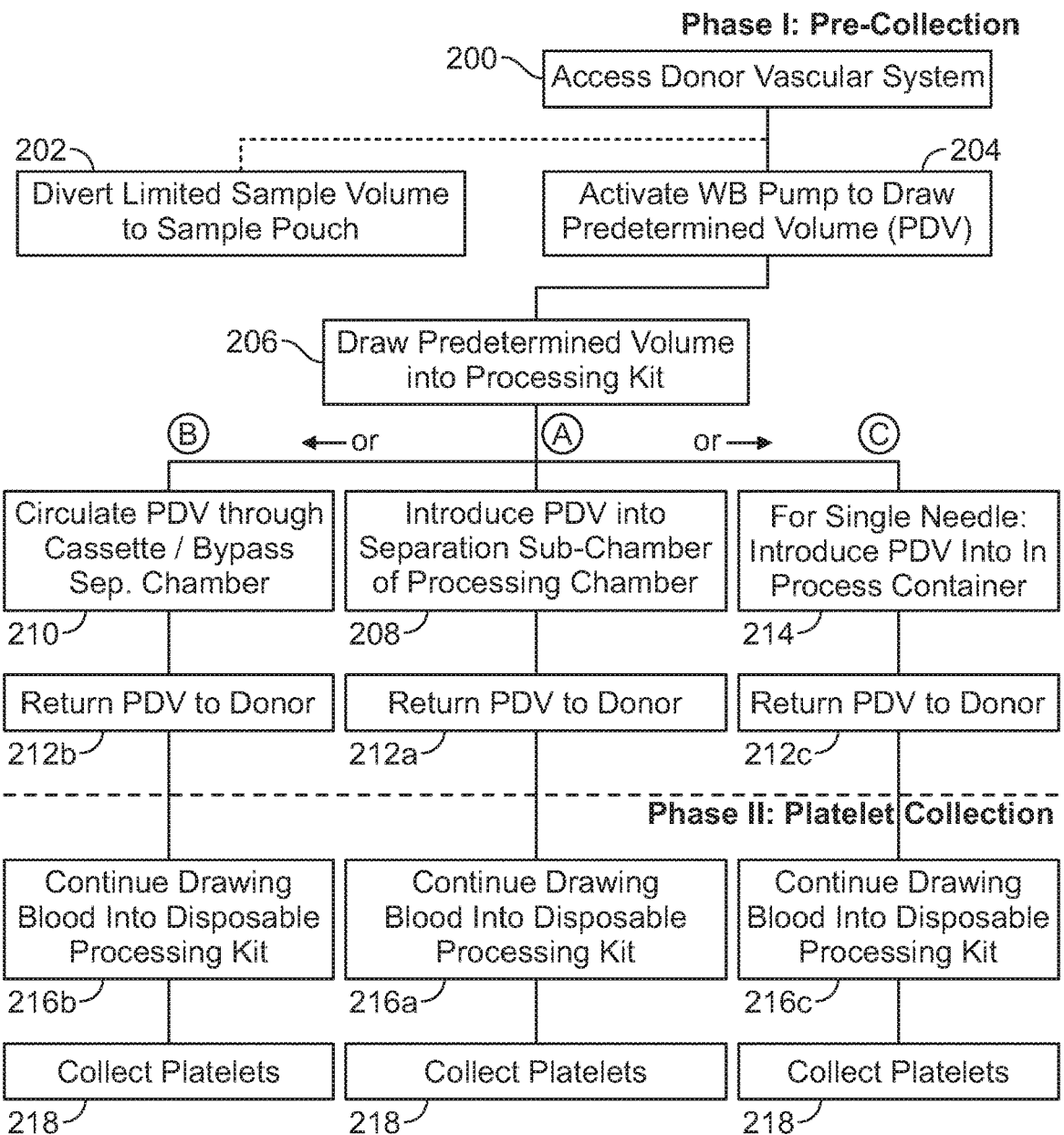
FIG. 9 is a flow chart setting forth the method(s) of reducing the risk of bacterial contamination of collected platelets in accordance with the present disclosure.

In accordance with the present disclosure and with specific reference to FIG. 9, platelet collection is typically commenced by initial venipuncture to provide access to the donor's vascular system (step 200). Needle 14, shown in FIGS. 2 and/or 2A, may be used to access the vascular system of the donor by puncturing the skin of the donor. In a two needle system (FIG. 2), venipuncture is performed on both arms with needles 14 and 14a. Preferably, with the system's pumps turned off, a small volume of whole blood may be drained from the donor through inlet needle 14 into sample pouch 35 (see FIGS. 2 and 2A). In an embodiment, typically approximately 20 to 35 ml of whole blood may be drained from the donor through inlet needle 14 into sample pouch 35. Diversion of this incoming volume of whole blood is believed to reduce the risk of contamination by bacteria that may have resided on the skin of the donor. See "Limiting and detecting bacterial contamination of apheresis platelets: inlet-line diversion and increased culture volume improve component safety;" Transfusion, 2009, August; 49(8): 1554-63; Eder AF et al. (The risk of contamination from venipuncture by return needle 14a is significantly less or substantially non-existent.)

To further reduce the risk of bacterial contamination of the collected platelets, a pre-determined volume of whole blood may be processed in accordance with the method and/or using the systems described herein and as set forth in FIG. 9. More particularly, in an initial pre-collection processing phase (Phase I, i.e., the steps above), a pre-determined volume of whole blood can be withdrawn and processed without subjecting the whole blood to the separation and collection (or concentration) steps that are typical in platelet collection procedures. Rather than separating the platelets from the whole blood so as to collect them in a collection sub-chamber 64, in Phase I, as shown in FIG. 9, an initial pre-determined volume (PDV) of whole blood can be processed in a way that does not result in the collection of platelets. In one embodiment, the pre-determined volume of whole blood may instead be returned to the donor, bypassing the steps of concentration and collection of the platelets and thereby keeping any potential residual contaminants out of the collected platelet product.

Thus, as shown in FIG. 9, after venipuncture by needle 14 and (optional) sample collection in sample pouch 35 (step 202), the controller (e.g., controller 300) activates rotation of whole blood (WB) pump 92a (step 204) to withdraw a pre-determined volume of whole blood from the donor (step 206). In accordance with the method labeled "A" in FIG. 9, the pre-determined volume is delivered into the first sub-chamber 62 of processing chamber 34 (step 208). The pre-determined volume of whole blood is allowed to accumulate in sub-chamber 62 and will eventually exit through red blood cell port 70, as previously described above.

During introduction of whole blood into processing chamber 34, the centrifuge bowl and spool 56 (with processing chamber 34 mounted thereon) may be spinning or stationary. In one embodiment, where the centrifuge bowl and spool 56 are spinning, some separation between platelet-rich plasma and red blood cells may occur. The spinning action of the centrifuge drives the platelet-rich plasma toward the "low g" wall, while the red blood cells, being denser, are driven toward the "high g" wall. However, in accordance with one embodiment of the present method, during this initial pre-collection Phase I, only the whole blood pump 92a (lower pump associated with cassette 16) may be activated by the controller (and not, for example, platelet-rich plasma pump 92a associated with right cassette 16b). Accordingly, the red blood cells and platelet-rich plasma (assuming some separation has occurred as a result of the spinning action of the centrifuge) will be withdrawn through red blood cell outlet port 70 and returned to the donor (step 212a).

In an alternative embodiment, both the whole blood pump 92a (associated with cassette 16) and platelet-rich plasma pump 92e (associated with cassette 16b) may be activated. In this scenario, the separated red blood cells may exit through red blood cell port 70 and be returned to the donor, whereas the platelet-rich plasma may be directed to the exit port 68 along the "low g" wall and withdrawn under the action of the platelet-rich pump. However, instead of being expressed to the second sub-chamber 64 of processing chamber 34, under the action of controller, the flow of platelet-rich plasma may be re-routed by selectively opening and closing internal flow paths within cassettes 16, 16a, and/or 16b to likewise return the platelet-rich plasma to the donor (also step 212a).

Thus, in either of the above-described return scenarios, and in contrast to the typical step of separating and collecting platelets wherein the platelet-rich plasma pump moves platelet-rich plasma from first sub-chamber 62 to second sub-chamber 64, under the action of the controller, valves and flow paths may be opened and closed and pumps may be activated or idled such that the platelet-rich plasma withdrawn from first sub-chamber 62 is returned to the donor rather than directed or transferred to second sub-chamber 64 for further separation and collection of platelets.

In another embodiment, also depicted in FIG. 9 and identified as method "B," the controller may be programmed to process the pre-determined volume of whole blood during Phase I completely outside of the processing chamber 34. For example, the pre-determined volume of whole blood may be withdrawn from the donor, as described above (steps 204, 206). The controller which has been programmed to open and close valve stations 110 in cassette 16 causes the pre-determined volume of whole blood to be circulated entirely through cassette 16, without ever reaching the processing chamber 34 (step 210). By selectively opening and closing the flow paths in cassette 16, the pre-determined volume may be returned to the donor (step 212b) through needle 14a (of a two needle fluid circuit) without ever being introduced into the processing chamber 34.

In another embodiment, identified as method "C," and also depicted in FIG. 9, where a single needle disposable fluid circuit of the type shown in FIG. 2A is used for both alternating withdrawal and return of whole blood and its components, the pre-determined volume of whole blood may be withdrawn and introduced into a "in process" container (step 214). The "in process" container serves as a temporary holding container for the pre-determined volume of blood. Once the controller has detected that the selected pre-determined volume of whole blood has been delivered to the "in process" container (either by pump revolutions or weight of the "in process" container), the controller activates the necessary pumps to pump the pre-determined volume from the "in process" container back to the donor. Once returned, the controller then initiates Phase II, i.e., the withdrawal of an additional volume of whole blood (step 216) from the donor for the ultimate processing, separation, and collection of platelets (step 218).

Controller 300 may be programmed to monitor flow rates and fluid volumes either by pump revolutions or in other ways to determine whether the pre-determined volume has been withdrawn from the donor. Once the pre-determined volume has been withdrawn, the controller is programmed to activate the platelet-rich plasma pump 92 associated with right cassette 16b and commence the processing of whole blood for the actual separation and collection of platelets (i.e., Phase II of FIG. 9).

In accordance with the present disclosure, the pre-determined volume of whole blood that is initially withdrawn from the donor prior to collection may be any volume that is deemed sufficient to further reduce the risk of bacterial contamination. A balance between a volume that provides a high degree of certainty as to the reduced risk of bacterial contamination on the one hand and the addition of time to the overall procedure on the other hand is preferred. In an embodiment, the pre-determined volume may be anywhere between about 100 and 150 ml of whole blood. More preferably, the pre-determined volume may be about 135 ml of whole blood. The method of reducing the risk of bacterial contamination described herein may be used in conjunction with or independent of the traditional sample diversion methods/systems that utilize a sample pouch (such as pouch 35.) More or less whole blood may be withdrawn as part of the pre-collection processing (Phase I, FIG. 9) of the pre-determined volume of whole blood, depending on the desired degree of confidence that no bacterial contamination from the needle stick is present in the collected platelets. In accordance with the present disclosure, the risk of bacterial contamination in the collected platelets can be reduced by over 50% and, depending upon the volume processed, up to 90-98% without adding significant time to the platelet collection procedure.

It will be understood that the embodiments described above are illustrative of some of the applications of the principles of the present subject matter. Numerous modifications may be made by those skilled in the art without departing from the spirit and scope of the subject matter disclosed herein, including those combinations of features that are individually disclosed or claimed herein. For these reasons, the scope hereof is not limited to the above description.

The invention claimed is:

1. A method for reducing the risk of bacterial contamination in collected blood platelets comprising:
 a) inserting a needle of a blood processing kit into a donor to access the vascular system of the donor;
 b) withdrawing a first pre-determined volume of whole blood from said donor, said volume being selected to reduce the risk of bacterial contamination;
 c) introducing said first pre-determined volume of said whole blood into at least a portion of said blood processing kit;
 d) returning said first pre-determined volume to said donor; and
 e) withdrawing a second volume of whole blood from said donor after returning said pre-determined first volume to said donor.

2. The method of claim 1 further comprising separating and collecting platelets only from said second volume of whole blood.

3. The method of claim 1 further comprising collecting a portion of whole blood from said donor in a sample collection container prior to withdrawing said first pre-determined volume of whole blood.

4. The method of claim 3 further comprising introducing a portion of said first pre-determined volume whole blood into a different portion of said blood processing kit.

5. The method of claim 1 comprising introducing said first pre-determined volume of said whole blood into a chamber of a multi-chambered blood processing container comprising first and second sub-chambers in fluid communication with one another.

6. The method of claim 5 comprising removing said first pre-determined volume from said one sub-chamber of said multi-chambered blood processing container without said first pre-determined volume entering said second sub-chamber.

7. The method of claim 6 comprising preventing said first pre-determined volume from entering said second chamber of said multi-chambered blood processing container.

8. The method of claim 1 comprising separating said first pre-determined volume of whole blood into red blood cells and platelet rich plasma and returning said red blood cells and said platelet-rich plasma to said donor.

9. The method of claim 8 comprising separating said red blood cells and platelet-rich plasma from said red blood cells by rotating said multi-chambered blood processing container.

10. The method of claim 1 wherein said first pre-determined volume of whole blood comprises about 100-150 ml.

11. The method of claim 3 wherein said portion of said whole blood collected in said sample collection container comprises about 20-35 ml.

12. The method of claim 1 further comprising returning said first pre-determined volume to said donor through a different needle providing access to the vascular system of said donor.

13. The method of claim 2 wherein the risk of bacterial contamination to the collected platelets is reduced by more than 50%.

14. The method of claim 13 wherein the risk of bacterial contamination to the collected platelets is reduced by up to 95%.

* * * * *